(12) United States Patent
Takata

(10) Patent No.: US 11,723,889 B2
(45) Date of Patent: Aug. 15, 2023

(54) AMYLOID FIBER FORMATION LIMITER OR INHIBITOR

(71) Applicants: Omoidesouzou Co., Ltd., Tokyo (JP); Hideyasu Takata, Saitama (JP); Tsukasa Takemura, Saitama (JP)

(72) Inventor: Hideyasu Takata, Saitama (JP)

(73) Assignees: Hideyasu Takata; OMOIDESOUZOU CO., LTD.; Tsukasa Takemura

( * ) Notice: Subject to any disclaimer, the term of this patent is extended or adjusted under 35 U.S.C. 154(b) by 240 days.

(21) Appl. No.: 17/179,462

(22) Filed: Feb. 19, 2021

(65) Prior Publication Data

US 2021/0169834 A1 Jun. 10, 2021

Related U.S. Application Data

(62) Division of application No. 15/305,114, filed as application No. PCT/JP2015/002067 on Apr. 14, 2015.

(30) Foreign Application Priority Data

Apr. 24, 2014 (JP) .................................. 2014-090476

(51) Int. Cl.
*A61K 31/196* (2006.01)
*A61K 9/00* (2006.01)

(52) U.S. Cl.
CPC .......... *A61K 31/196* (2013.01); *A61K 9/0053* (2013.01)

(58) Field of Classification Search
CPC ..... A61K 31/196; A61K 9/0053; A61P 17/00; A61P 25/28; A61P 43/00
See application file for complete search history.

(56) References Cited

U.S. PATENT DOCUMENTS

2009/0312422 A1   12/2009   Weller et al.

FOREIGN PATENT DOCUMENTS

| CA | 2244679 | 8/1997 |
| JP | 2009120607 | 6/2009 |
| WO | 9806403 A1 | 2/1998 |
| WO | 2009024543 A1 | 2/2009 |

OTHER PUBLICATIONS

Miyoshi et al., Dermatologic Disease Treatment, vol. 22(5), pp. 441-444, publ. 2000 (Year: 2000).*
Miyoshi et al., Dermatologic Disease Treatment, vol. 22(5), pp. 441-444, publ. 2000; English translation (Year: 2000).*
Blanchard, B. et al. "Efficient reversal of Alzheimer's disease fibril formation and elimination of neurotoxicity by a small molecule" PNAS, Oct. 5, 2004, vol. 101, No. 40, pp. 14326-14332.
Chiti F. et al. "Amyloid formation by globular proteins under native conditions" Nat Chem Biol. Jan. 2009; 5(1):15-22. doi: 10.1038/nchembio.131.
Connors, C. et al. "Tranilast Binds to Alpha Beta Monomers and Promotes Alpha Beta Fibrillation" Biochemistry 2013, 52 3995-4002.
Extended European Search Report (EP 15782806.2) dated Sep. 1, 2017.
Hamley, L.W. "The Amyloid Beta Peptide: A Chemist's Perspective. Role in Alzheimer's and Fibrillization" Chemical Reviews, 2012, American Chemical Society, val. 112, pp. 5147-5192.
Hammarström P. et al. "Trans-suppression of misfolding in an amyloid disease" Science. Seo, 28, 2001;293(5539):2459-62.
Howlett, D. et al. "Hemin and related porphyrins inhibit beta-amyloid aggregation" FEBS Letters 417 (1997) 249-251.
International Preliminary Report on Patentability [PCT/JP2015/002067] dated Nov. 3, 2016.
Joji Jidoi et al., Dermatology region, Nippon Rinsho, 1991, vol. 49, No. 4, p. 179-182.
Kato, Y. et al., "A case of secondary amyloidosis exhibiting an idiosyncraic form" Japan Cornea Conference 2012 Program Abstracts, 2012, p. 69.
Kayed, R. et al. "Common structure of soluble amyloid oligomers implies common mechanism of pathogenesis" Science. Apr. 18, 2003;300(5618):486-9.
Li, J. et al. "Dopamine and L-dopa disaggregate amyloid fibrils: implications for Parkinson's and Alzheimer's disease" FASEB J. Jun. 2004;18(9):962-4. Epub Apr. 1, 2004.
Lorenzo, A. et al. "Beta-Amyloid neurotoxicity requires fibril formation and is inhibited by Congo red" Proc. Nati. Acad. Sci. USA vol. 91, pp. 12243-12247, Dec. 1994.
Masamitsu Nakazato, Familial amyloid polyneuropathy, Separate volume/Igakuno Ayumi (Journal of Clinical and Experimental Medicine Nerve disease—State of arts, Ver. 1, 1999, p. 555 559.
Miyoshi, K et al. "Amyloid Taisen" Practical Dermatology, 2000, vol. 22, No. 5, pp. 441-444.
Office Action JP 2016-514694 dated Jun. 28, 2018.
Ono, K. et al. "Anti-amyloidogenic activity of tannic acid and its activity to destabilize Alzheimer's beta-amyloid fibrils in vitro" Biochimica et Biophysica Acta 1690 (2004) 193-202.

(Continued)

*Primary Examiner* — Sarah Pihonak
(74) *Attorney, Agent, or Firm* — Edwin S. Flores; Daniel J. Chalker; Chalker Flores, LLP

(57) ABSTRACT

The object of the present invention is to provide a formulation with the effect of effectively suppressing or inhibiting amyloid fibril formation by the dissolution, elimination (discharge), etc. of amyloid fibril formation in vivo.
If an agent for suppressing or inhibiting an amyloid fibril formation comprising tranilast or a pharmacologically acceptable salt thereof as an active ingredient is administered by a method such as oral administration, amyloid fibril formation can be effectively suppressed or inhibited in vivo as a result of effects such as amyloid fibril dissolution or elimination (discharge). Therefore, it is possible to prevent or treat amyloid plaques, in which amyloid fibrils formed by the aggregation of amyloid protein have been deposited, and to prevent or treat diseases arising from amyloid fibril deposition, that is, diseases arising from the deposited amyloid fibrils themselves and diseases that cause dysfunction of organs or tissues as a result of amyloid fibril deposition.

12 Claims, 2 Drawing Sheets

(56) References Cited

OTHER PUBLICATIONS

Ono, K. et al. "Curcumin has potent anti-amyloidogenic effects for Alzheimer's beta-amyloid fibrils in vitro" J Neurosci Res. Mar. 15, 2004;75(6):742-50.

Pappolla, M. et al. "Inhibition of Alzheimer beta-Fibrillogenesis by Melatonin" The Journal of Biological Chemistry, vol. 273, No. 13, Issue of Mar. 27, 1998, pp. 7185-7188.

Perfetto et al. "Systemic amyloidosis: a challenge for the rheumatologist" Nature Reviews Rheumatology, 2010, Nature Publishing Group, val. 6, pp. 417-429.

Satoshi Dekio, Skin amyloidosis, Nippon Rinsho (Separate volume), Region-wise syndrome series 22, Blood syndrome III, 1998, p. 511-514.

Tsai, J. et al. "Fibrillar amyloid deposition leads to local synaptic abnormalities and breakage of neuronal branches" Nat Neurosci. Nov. 2004;7(11):1181-3. Epub Oct. 10, 2004.

Wood, S. et al. "Selective Inhibition of Alpha beta Fibril Formation" The Journal of Biological Chemistry vol. 271, No. 8, Issue of Feb. 23, pp. 4086-4092, 1996.

* cited by examiner

AMYLOID FIBER FORMATION LIMITER OR INHIBITOR

CROSS-REFERENCE TO RELATED APPLICATIONS

This application is a divisional of U.S. patent application Ser. No. 15/305,114 filed on Oct. 19, 2016, which is the National Stage of International Application No. PCT/JP2015/002067, filed on Apr. 14, 2015 claiming the priority of JP 2014-090476, filed on Apr. 24, 2014, the content of each of which is incorporated by reference herein.

TECHNICAL FIELD OF THE INVENTION

The present invention relates to a formulation for suppressing or inhibiting an amyloid fibril formation with the effect of dissolving or eliminating (discharging) amyloid fibrils, comprising tranilast or a pharmacologically acceptable salt thereof as an active ingredient, to an agent for preventing or treating an amyloid plaque comprising said formulation, or to an agent for preventing or treating amyloidosis comprising said formulation.

STATEMENT OF FEDERALLY FUNDED RESEARCH

None.

INCORPORATION-BY-REFERENCE OF MATERIALS FILED ON COMPACT DISC

None.

BACKGROUND OF THE INVENTION

Amyloid fibril is a fibrous supramolecular polymer formed by the aggregation of misfolded proteins. Pathologically, amyloid fibrils are stained orange-red with alkaline Congo red staining, show green birefringence in the observation using a polarizing microscope, and show an unbranched fibrous structure with a width of 7 to 15 nm in the observation using an electronic microscope.

Amyloidosis is a collective term for the diseases that cause dysfunction due to amyloid fibril deposition in organs or tissues that works continuously or in organs or tissues that are affected with a debilitating disease. In 1980, Glenner, G. C. showed that proteins (amyloid protein) constituting amyloid fibrils that are specific to each disease form amyloid fibrils abundant with a β-sheet structure and cause a deposition, and thereafter, there has been a variety of reports on the association between amyloid proteins and diseases. For example, an association between an amyloid fibril composed of amyloid and diseases such as Alzheimer's type senility, Down syndrome; an association between an amyloid fibril composed of α-synuclein and diseases such as Parkinson's disease, Lewy body type senility, multiple system atrophy; an association between an amyloid fibril composed of prion and diseases such as Creutzfeldt-Jakob disease, Gerstmann-Sträussler syndrome, mad cow disease; and an association between an amyloid fibril composed of tau and diseases such as Alzheimer's type senility, FTDP-17, progressive supranuclear palsy, corticobasal degeneration, Pick's disease have been reported (Non-Patent Document 1).

It is believed that, besides amyloid fibril deposition itself, intermediate molecules such as oligomers or protofibrils, which are involved in amyloid fibril formation, are one of the causes of cell death or cellular disorder (Non-Patent Documents 2, 3). Therefore, it is believed that amyloidosis can be treated by suppressing amyloid fibril formation to increase the instability of the proteins constituting amyloid fibrils (Non-Patent Document 4).

Until now, clioquinol (Patent Document 1), curcumin (Non-Patent Document 5), tannic acid (Non-Patent Document 6), hemin (Non-Patent Document 7), melatonin (Non-Patent Document 8), 4,5-dianilinophthalimide (Non-Patent Document 9), L-DOPA (Non-Patent Document 10), hexadecyl-N-methylpiperidinium (Non-Patent Document 11), congo red, which is a fluorescent stain (Non-Patent Document 12), etc. have been reported as compounds for suppressing amyloid fibril formation.

On the other hand, tranilast is a compound that has already been commercially supplied form Kissei Pharmaceutical Co., Ltd. as an antiallergic drug "Rizaben", and has been reported as showing good drug efficacy against keloid, hypertrophic scar (Non-Patent Documents 13, 14). However, it has not been known whether tranilast has an effect of suppressing amyloid fibril formation.

SUMMARY OF THE INVENTION

Object to be Solved by the Invention

The object of the present invention is to provide a formulation with the effect of effectively suppressing or inhibiting amyloid fibril formation by the dissolution or elimination (discharge), etc. of an amyloid fibril in vivo.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1A:
FIGS. 1A-1H are figures showing improvement in symptoms achieved by administering tranilast to a patient with cutaneous lichen amyloidosis (Case 2).

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Means to Solve the Object

The present inventor has been extensively investigating to solve the above-described problems. During the process, it was investigated whether amyloid deposition in the skin could be reduced or whether cutaneous lichen amyloidosis could be treated by using tranilast (brand name: Rizaben) known as a therapeutic agent for atopic dermatitis, and it was found that the amyloid fibril formation was suppressed and the function of skin could be improved upon the administration of tranilast. Further, based on the finding, it was investigated whether dementia arising from amyloid fibril deposition could be ameliorated and it was confirmed that clear ameliorating effect was observed upon the administration of tranilast. The present invention has been thus completed based on these findings.

Specifically, the present invention relates to (1) an agent for suppressing or inhibiting an amyloid fibril formation, comprising tranilast or a pharmacologically acceptable salt thereof as an active ingredient, (2) the agent according to (1), wherein the agent is administered orally, (3) the agent according to (1) or (2), wherein the agent has an effect of dissolving or discharging an amyloid fibril.

Further, the present invention relates to (4) an agent for preventing or treating an amyloid plaque, comprising the agent according to any one of (1)-(3), (5) the agent according to (4), wherein the amyloid plaque is in the brain, (6) the agent according to (4), wherein the amyloid plaque is in the skin.

Further, the present invention relates to (7) an agent for preventing or treating an amyloidosis, wherein the agent comprises the agent according to any one of (1)-(3), (8) the agent according to (7), wherein the amyloidosis is cerebral amyloidosis, (9) the agent according to (8), wherein the cerebral amyloidosis is dementia arising from the deposition of an amyloid fibril in the brain, (10) the agent according to (7), wherein the amyloidosis is cutaneous amyloidosis, (11) the agent according to (10), wherein the cutaneous amyloidosis is cutaneous lichen amyloidosis.

Examples of still another embodiment of the present invention can include a method for preventing or treating amyloid plaques or a method for preventing or treating diseases arising from amyloid fibril deposition (diseases arising from the deposited amyloid fibrils themselves and diseases that cause dysfunction of organs or tissues as a result of amyloid fibril deposition), by administering an agent for suppressing or inhibiting an amyloid fibril formation comprising tranilast or a pharmacologically acceptable salt thereof as an active ingredient to a patient in need of suppressing or inhibiting of amyloid fibril formation.

Examples of still another embodiment of the present invention can include tranilast or a pharmacologically acceptable salt thereof for use as an agent for suppressing or inhibiting an amyloid fibril formation, tranilast or a pharmacologically acceptable salt thereof for use as an agent for preventing or treating an amyloid plaque, or tranilast or a pharmacologically acceptable salt thereof for use as an agent for preventing or treating an amyloidosis.

Examples of still another embodiment of the present invention can include the use of tranilast or a pharmacologically acceptable salt thereof in the manufacture of an agent for suppressing or inhibiting an amyloid fibril formation, the use of tranilast or a pharmacologically acceptable salt thereof in the manufacture of an agent for preventing or treating an amyloid plaque, or the use of tranilast or a pharmacologically acceptable salt thereof in the manufacture of an agent for preventing or treating amyloidosis.

The agent for suppressing or inhibiting an amyloid fibril formation of the present invention comprises tranilast or a pharmacologically acceptable salt thereof (hereinafter referred to collectively as "tranilasts") as an active ingredient, and, if necessary, compounding ingredients can further be added, such as a pharmaceutically acceptable common carrier, a binder, a stabilizer, an excipient, a diluent, a pH buffering agent, a disintegrator, an isotonic agent, an additive, a coating, a solubilizer, a lubricating agent, a sliding agent, a solubilizing agent, a lubricant, a seasoning, a sweetening agent, a solvent, a gelatinizer, and a nutrient. Specific examples of such compounding ingredients can include water, physiological saline, animal fat and oil, vegetable oil, lactose, starch, gelatin, crystalline cellulose, gum, talc, magnesium stearate, hydroxypropylcellulose, polyalkylene glycol, polyvinyl alcohol, and glycerin.

The agent for suppressing or inhibiting an amyloid fibril formation of the present invention has an effect of suppressing or inhibiting amyloid fibril formation in vivo. The effect of suppressing or inhibiting amyloid fibril formation in vivo can include for example, in cells or tissues in which amyloid fibrils have been deposited, an effect of suppressing the production of a protein constituting an amyloid fibril (amyloid protein), an effect of suppressing the aggregation of an amyloid protein, an effect of degradation of an amyloid protein, an effect of dissolving (degradation of) an amyloid fibril (structure), and an effect of discharging an amyloid protein or an amyloid fibril to the outside of said cells or tissues. The effect of dissolution (degradation) of an amyloid fibril (structure) and the effect of discharging an amyloid protein or an amyloid fibril to the outside of said cells or tissues are preferable.

In the present invention, "amyloid fibril" refers to a fibrous supramolecular polymer formed by the aggregation of misfolded (high-ordered-structure abnormally formed) proteins (amyloid protein) and has the structure which is abundant with a β-sheet. Examples of the above-described amyloid protein can include proteins such as amyloid β, tau, immunoglobulin light chain, amylin, amyloid A, transthyretin, lysozyme, BriL, cystatin C, scrapie, β2 microglobulin, apolipoprotein A1, gelsolin, islet amyloid, fibrinogen, prolactin, insulin, calcitonin, keratin, atrial natriuretic peptide, α-synuclein, prion, huntingtin, superoxide dismutase, neuroserpin, α1-antichymotrypsin.

Tranilast of the present invention is N-(3,4-dimethoxycinnamoyl)anthranilic acid and is a compound represented by the chemical structural formula shown below.

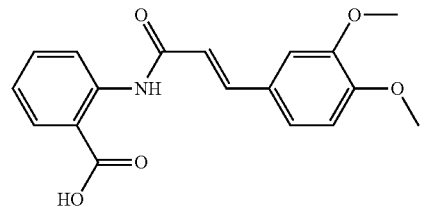 [SMILES: COc1ccc(/C=C/C(=O)Nc2ccccc2C(=O)O)cc1OC]

Examples of pharmacologically acceptable salt of tranilast of the present invention include a metal salt formed from aluminum, calcium, lithium, magnesium, potassium, sodium, and zinc, and an organic salt formed from N,N'-dibenzylethylenediamine, chloroprocaine, choline, diethanolamine, ethylenediamine, N-methylglucamine, lysine, procaine, etc.

The agent for preventing or treating an amyloid plaque of the present invention and the agent for preventing or treating an amyloidosis of the present invention are not particularly limited as long as they comprise an agent for suppressing or inhibiting an amyloid fibril formation of the present invention, that is, as long as they comprise tranilasts as an active ingredient for the effect of suppressing or inhibiting amyloid fibril formation, and examples include those further added with compounding ingredients such as a pharmaceutically acceptable common carrier, a binder, a stabilizer, an excipient, a diluent, a pH buffering agent, a disintegrator, an isotonic agent, an additive, a coating, a solubilizer, a lubricating agent, a sliding agent, a solubilizing agent, a lubricant, a seasoning, a sweetening agent, a solvent, a gelatinizer, and a nutrient. Specific examples of such compounding ingredients can include water, physiological saline, animal fat and oil, vegetable oil, lactose, starch, gelatin, crystalline cellulose, gum, talc, magnesium stearate, hydroxypropylcellulose, polyalkylene glycol, polyvinyl alcohol, and glycerin.

Examples of the dosage form of the agent for suppressing or inhibiting an amyloid fibril formation of the present invention, of the agent for preventing or treating an amyloid plaque of the present invention, and of the agent for preventing or treating an amyloidosis of the present invention can include oral administration in drug forms such as powder, granule, tablet, capsule, syrup, or suspension, and parenteral administration including injection in a drug form such as solution, emulsion, or suspension, administration in a drug form of transdermal agent to the skin, administration to the eyes in a drug form of eye drops, or nasal administration in a drug form such as nasal drops, nasal sprays, and oral administration is preferable.

The dosage of tranilasts in the agent for suppressing or inhibiting an amyloid fibril formation of the present invention, tranilasts in the agent for preventing or treating an amyloid plaque of the present invention, and tranilasts in the agent for preventing or treating an amyloidosis of the present invention is determined as appropriate depending on age, body weight, gender, symptom, susceptibility to drug, etc. Usually, the agent is administered in a dosage range of 1 mg to 30 g/day, preferably in a dosage range of 10 to 3000 mg/day, more preferably in a dosage range of 50 to 2000 mg/day, still preferably in a dosage range of 100 to 1000 mg/day, still more preferably in a dosage range of 200 to 600 mg/day, once or more than once (e.g., two to four times) in divided doses per day, however, the dosage may be adjusted depending on the state of symptom improvement. Tranilasts, that are the active ingredient of the present invention, are a drug (brand name: Rizaben [RIZABEN]) that has already been used for patients with atopic dermatitis, and the usage and the side effects thereof are well known. Therefore, the dosage and the dosage form can be selected based on experiences when using the agent for suppressing or inhibiting an amyloid fibril formation of the present invention, the agent for preventing or treating an amyloid plaque of the present invention, and the agent for preventing or treating an amyloidosis of the present invention.

An amyloid fibril that is the application for the agent for suppressing or inhibiting an amyloid fibril formation of the present invention is not particularly limited as long as it is an amyloid fibril formed in organs or tissues; further, an amyloid plaque that is the application for the agent for preventing or treating an amyloid plaque of the present invention is not particularly limited as long as it is an amyloid plaque in which amyloid fibrils formed by the aggregation of amyloid protein in organs or tissues have been deposited; further, amyloidosis that is the application for the agent for preventing or treating an amyloidosis of the present invention is not particularly limited as long as it is a disease arising from amyloid fibril deposition (diseases arising from deposited amyloid fibrils themselves and diseases that cause dysfunction of organs or tissues as a result of amyloid fibril deposition); wherein examples of the organs or tissues can include brain, lung, liver, kidney, heart, intestine (large intestine, small intestine, colon, etc.), pancreas, bone (bone marrow), skin, etc. and among these brain or skin can be preferably exemplified.

Any method may be used for detecting amyloid plaques. For example, of amyloid plaques in the brain, the amyloid plaques composed of amyloid β (senile plaques) can be detected by a method using 11C labeled PIB (Pittsburgh Compound-B) deposited in said part (Japanese Unexamined Patent Application Publication (Translation of PCT Application) No. 2004-506723) and a device (PET-CT) for investigations by Positron Emission Tomography (PET; Positron Emission Tomography) and Computerized Tomography (CT; Computerized Tomography) simultaneously. Further, amyloid plaques in the skin can be detected as punctate brown pigmented spots formed in *crista* cutis (a raised portion between skin grooves) except follicle. Here, said punctate brown pigmented spot is characteristic in that the punctate pigmented spots with a diameter of 2 to 3 mm are linearly arranged, and that looks ripple like arrangement.

Examples of the above-described amyloidosis can include, specifically, systemic amyloidosis such as immune cellular amyloidosis (e.g., AL amyloidosis, AH amyloidosis), reactive AA amyloidosis (secondary amyloidosis), familial amyloidosis (e.g., Familial Amyloid Polyneuropathy [FAP] I, FAPII, FAPIII, FAPIV, Familial Mediterranean fever [FMF], Muckle-Wells syndrome), dialysis amyloidosis, senile TTR amyloidosis, and localised amyloidosis such as cerebral amyloidosis, endocrine amyloidosis (medullary thyroid cancer, diabetes mellitus type 2, insulinoma, isolated atrial amyloid), cutaneous amyloidosis, nodular localised amyloidosis, and among these cerebral amyloidosis or cutaneous amyloidosis can be preferably exemplified.

Examples of the above-described cerebral amyloidosis can include, specifically, cerebral amyloid angiopathy, hereditary cerebral hemorrhage (Dutch type or Icelandic type) arising from amyloid fibril deposition in the brain, and dementia arising from amyloid fibril deposition in the brain, and among these dementia arising from amyloid fibril deposition in the brain can be preferably exemplified. Said "dementia" can be exemplified by Alzheimer's type dementia (senility), dementia developed from Parkinson's disease, dementia developed from Down syndrome, dementia developed from prion diseases, Lewy bodies type dementia (senility), dementia developed from multiple system atrophy, dementia developed from Creutzfeldt-Jakob disease, dementia developed from Gerstmann-Sträussler syndrome, dementia developed from mad cow disease, dementia developed from FTDP-17, dementia developed from progressive supranuclear palsy, dementia developed from corticobasal degeneration, and dementia developed from Pick's disease.

Further, examples of the above-described cutaneous amyloidosis can include, specifically, friction melanosis, lichen (cutaneous lichen amyloidosis), macular (cutaneous macular amyloidosis), and anosacral cutaneous (anosacral cutaneous amyloidosis) arising from amyloid fibril deposition in the skin, and among these cutaneous lichen amyloidosis can be preferably exemplified.

The above-described tranilasts can be produced by any publicly known methods such as chemical synthesis, production by microorganisms, production by enzyme, however, commercially marketed products may also be employed. For example, commercially marketed products such as Rizaben capsule, Rizaben granules, Rizaben dry syrup (all from Kissei Pharmaceutical Co., Ltd.), Ainteru capsule 100 mg, Ainteru dry syrup (all from Choseido Pharmaceutical Co., Ltd.) are included.

The present invention is illustrated in detail with the following examples, however, the present invention is not limited to these examples.

Example 1

1. Confirmation that the agent for suppressing or inhibiting an amyloid fibril formation of the present invention has a therapeutic effect against cutaneous amyloidosis.

1-1 Case 1

A patient (N. Y., 60 years of age, female) observed with symptoms of cutaneous amyloidosis specific pigment-associating invasion and itch in the upper back had been treated without tranilast for an initial duration of 4 years, however, no therapeutic effect was observed. Therefore, the treatment shifted to the use of tranilast. The above-mentioned patient was administered orally with a 100 mg capsule of tranilast (brand name: Rizaben, Kissei Pharmaceutical Co., Ltd.) three times a day. About 1 month after the start of oral administration the pigmentation started to thin, and within another 1 month it was shown that itch was reduced and rash was largely ameliorated, with the gradual reduction of the level of pigmentation. Worsening or relapse of rash was not observed at least 3 years afterwards.

1-2 Case 2

Figure 1B:
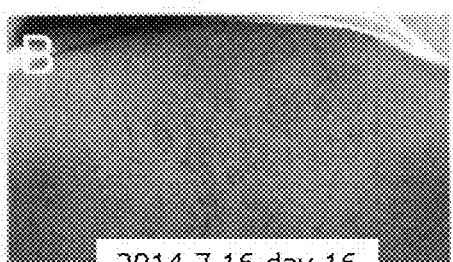
Figure 1C:
Figure 1D:
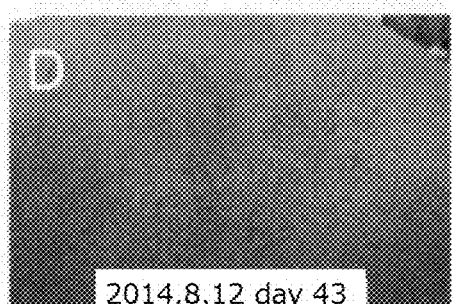
Figure 1E:
Figure 1F:
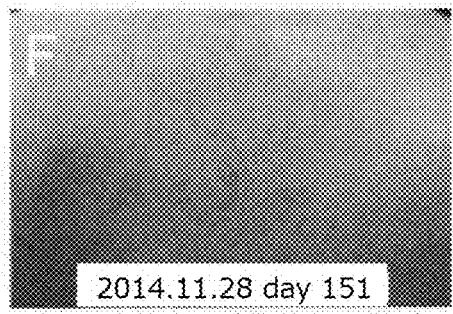
Figure 1G:
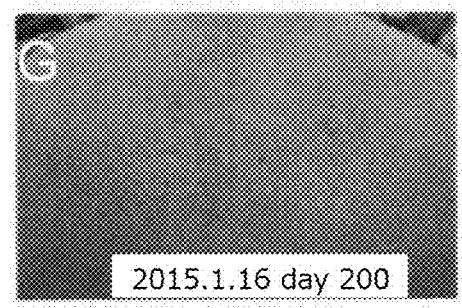
Figure 1H:

A patient observed with symptoms of typical amyloid lichen in the upper back (27 years of age, female, atopic dermatitis appeared in early life) was at first under treatment with difluprednate ointment (MYSER Ointment), which is a topical steroid categorized into "Very Strong: group II", however, amelioration was not observed. Therefore, the treatment shifted to the use of tranilast. The above-mentioned patient was administered orally with a 100 mg capsule of tranilast (brand name: Rizaben, Kissei Pharmaceutical Co., Ltd.) three times a day. From day 16 (Jul. 16, 2014) (see FIG. 1B) after the start of oral administration on Jun. 30, 2014 (see FIG. 1A), amyloid deposited brown papule was found to be thinned, decreased in size, and ameliorated clearly. The degree of amelioration of rash increased day by day (see FIGS. 1C to 1E). Amyloid deposited brown papule almost disappeared on day 151 (Nov. 28, 2014) (see FIG. 1F) after the start of oral administration, and the condition was maintained until at least day 238 (Feb. 23, 2015) (see FIG. 1H).

1-3 Case 3

Figure 2A:
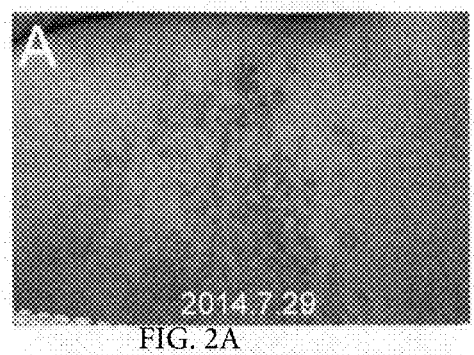
FIGS. 2A-2G are figures showing improvement in symptoms achieved by administering tranilast to a patient with cutaneous lichen amyloidosis (Case 3).
Figure 2B:
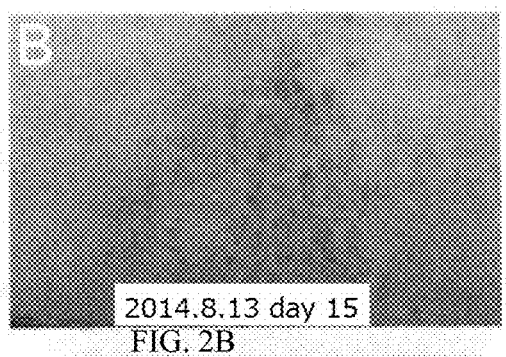
Figure 2C:
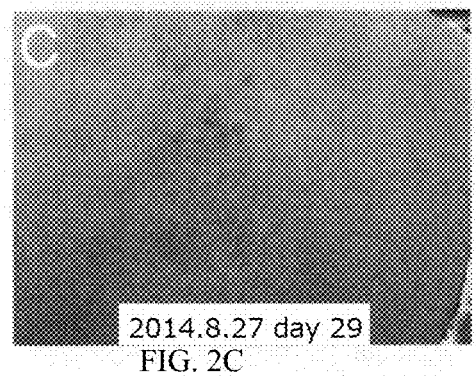
Figure 2D:
Figure 2E:
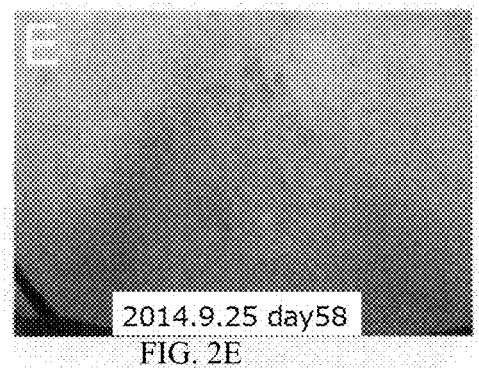
Figure 2F:
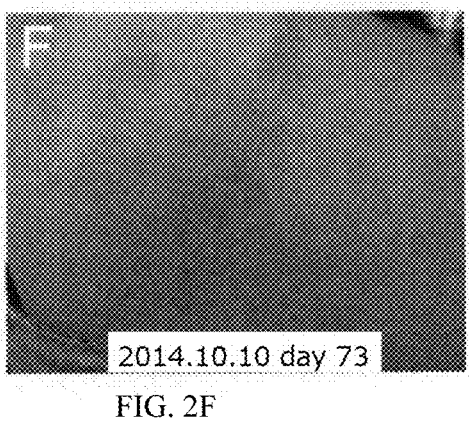
Figure 2G:

A patient (23 years of age, female) observed with chronic eczema with rash along with strong itch in the upper back for several years started the treatment with tranilast. The patient was administered orally with a 100 mg capsule of tranilast (brand name: Rizaben, Kissei Pharmaceutical Co., Ltd.) three times a day. When the oral administration started on Jul. 29, 2014, amyloid deposited brown papule was densely lichenified (see FIG. 2A). However, on day 15 (Aug. 13, 2014) (see FIG. 2B) after the start of oral administration, improvement in the symptoms was observed. Further, on day 29 (Aug. 27, 2014) (see FIG. 2C) after the start of oral administration, clear improvement in the symptoms was observed, and the improved condition was maintained afterwards until at least day 89 (Oct. 26, 2014) (see FIGS. 2D to 2G).

These results show that, in skin tissues or cells in which amyloid fibrils have been deposited, tranilast suppressed or inhibited amyloid fibril formation in skin tissues or cells and improved the function of the skin by suppressing the production of amyloid proteins such as keratin, by suppressing the aggregation of amyloid protein, by promoting the dissolution (degradation) of amyloid protein, or by promoting the discharge of amyloid protein to the outside of skin tissues or cells.

Example 2

2. Confirmation that the agent for suppressing or inhibiting an amyloid fibril formation of the present invention has a therapeutic effect against cerebral amyloidosis.

Because it was shown that tranilast has the effect of suppressing amyloid fibril formation in the skin, whether dementia and Alzheimer's disease arising from amyloid fibril deposition in the brain could be ameliorated was studied.

2-1 Case 4

A patient with dementia (H. Y., 79 years of age, male) was administered orally with a 100 mg capsule of tranilast (brand name: Rizaben, Kissei Pharmaceutical Co., Ltd.) three times a day. 1 year and 4 months after the start of administration of tranilast in August 2012, clear ameliorating effect was observed (see Table 1) by two types of testing methods for dementia (HDS-R [Hasegawa Dementia Scale-Revised] and MMSE [Mini-Mental State Examination]).

TABLE 1

| Start of Tranilast Administration | HDS-R Value | MMSE Value |
|---|---|---|
| 3 years and 10 months before (October 2008) | — | 28 |
| 1 year and 5 months before (March 2011) | 23 | 27 |
| start of the administration (August 2012) | — | — |
| 5 months after (January 2013) | 15 | 22 |
| 1 year and 4 months after (December 2013) | 20 | 25 |

2-2 Case 5

A patient with Alzheimer's disease (88 years of age, male) was administered orally with a 100 mg capsule of tranilast (brand name: Rizaben, Kissei Pharmaceutical Co., Ltd.) three times a day. About 5 months after the start of administration of tranilast on Oct. 11, 2014, clear ameliorating effect on the symptoms of Alzheimer's type dementia was observed (see Table 2) by two types of testing methods for dementia (HDS-R and MMSE).

TABLE 2

| Start of Tranilast Administration | HDS-R Value | MMSE Value |
|---|---|---|
| start of the administration (Oct. 11, 2014) | 9 | 14 |
| about 5 months after (Mar. 19, 2015) | 12 | 22 |

These results show that, in nerve tissues or cells in which amyloid fibrils have been deposited, tranilast suppressed or inhibited amyloid fibril formation in the nerve tissues or cells and improved the nerve function, by suppressing the production of amyloid proteins such as amyloid β, by suppressing the aggregation of amyloid proteins, by promoting the dissolution (break-down) of amyloid proteins, or by promoting the discharge of amyloid proteins to the outside of the nerve tissues or cells.

3. Summary

It has been known conventionally that if a certain tissue is chronically in a debilitating condition over long periods; for example, one suffers from a debilitating disease such as atopic dermatitis over long periods, amyloid fibrils deposit in the skin and refractory cutaneous lichen amyloidosis is caused. It is considered that tranilast acted such that it would effectively reduce the deposited amyloid fibrils in the skin or brain tissues in the hippocampus upon the systemic administration of tranilast to a patient with cutaneous lichen amyloidosis or a patient with dementia such as Alzheimer's type dementia with no improvement of symptoms observed with conventional treatments. That is, the treatment with tranilast is effective also in brain tissues and therefore it is considered that tranilast passed the blood-brain barrier.

INDUSTRIAL APPLICABILITY

The present invention can effectively suppress or inhibit amyloid fibril formation in vivo as a result of effects of tranilast, such as amyloid fibril dissolution or elimination (discharge). Therefore, the present invention is effective to prevent or treat amyloid plaques, and to prevent or treat diseases arising from amyloid fibril deposition (diseases arising from the deposited amyloid fibrils themselves and diseases that cause dysfunction of organs or tissues as a result of amyloid fibril deposition).

REFERENCES

Patent Documents

Patent Document 1: WO 98/06403

Non-Patent Documents

Non-Patent Document 1: Chiti, F. & Dobson, C. M. Nat. Chem. Biol. 5: 15-22 (2009)
Non-Patent Document 2: Kayed, R. et al., Science 300: 486-489 (2003)
Non-Patent Document 3: Tsai, J. et al., Nature Neuroscience 7: 1181-1183 (2004)
Non-Patent Document 4: Hammarstrom, P., Science 293: 2459-2462 (2001)
Non-Patent Document 5: Ono, K. et al., J. Neurosci. Res. 75: 742-750 (2004)
Non-Patent Document 6: Ono, K. et al., Biochim. Biophys. Acta, 1690: 193-202 (2004)
Non-Patent Document 7: Howlett, D. R. et al., FEBS Lett. 417: 249-251 (1997)
Non-Patent Document 8: Pappolla, M. et al., J. Biol. Chem. 273: 7185-7188 (1998)
Non-Patent Document 9: Blanchard, B. et al., Proc. Natl. Acad. Sci. USA. 101: 14326-14332 (2004)
Non-Patent Document 10: Li, J. et al., FASEB J. 18: 962-964 (2004)
Non-Patent Document 11: Wood, S. et al., J. Biol. Chem. 271: 4086-4092 (1996)
Non-Patent Document 12: Lorenzo, A. & Yankner, B. A., Proc. Natl. Acad. Sci. USA. 91: 12243-12247 (2004)
Non-Patent Document 13: Ichikawa K. et al., Ohyoyakuri (Pharmacometrics): 43(5) 401 (1992)
Non-Patent Document 14: Suzawa H., NihonYakurigaku-Zasshi (Folia Pharmacologica Japonica): 99(4) 231 (1992)

What is claimed is:

1. A method for treating an amyloid plaque in the skin comprising administering tranilast or a pharmacologically acceptable salt thereof which is the only active agent to a patient in need of treating amyloid plaque in the skin.

2. The method according to claim 1, wherein the tranilast or a pharmacologically acceptable salt thereof is administered orally.

3. The method according to claim 1, wherein the tranilast or a pharmacologically acceptable salt thereof has an effect of dissolving or discharging an amyloid fibril.

4. The method according to claim 2, wherein the tranilast or a pharmacologically acceptable salt thereof has an effect of dissolving or discharging an amyloid fibril.

5. A method for treating a cutaneous amyloidosis comprising administering tranilast or a pharmacologically acceptable salt thereof which is the only active agent to a patient in need of treating cutaneous amyloidosis.

6. The method according to claim 5, wherein the tranilast or a pharmacologically acceptable salt thereof is administered orally.

7. The method according to claim 5, wherein the tranilast or a pharmacologically acceptable salt thereof has an effect of dissolving or discharging an amyloid fibril.

8. The method according to claim 6, wherein the tranilast or a pharmacologically acceptable salt thereof has an effect of dissolving or discharging an amyloid fibril.

9. The method according to claim 5, wherein the cutaneous amyloidosis is cutaneous lichen amyloidosis.

10. The method according to claim 6, wherein the cutaneous amyloidosis is cutaneous lichen amyloidosis.

11. The method according to claim 7, wherein the cutaneous amyloidosis is cutaneous lichen amyloidosis.

12. The method according to claim 8, wherein the cutaneous amyloidosis is cutaneous lichen amyloidosis.

* * * * *